United States Patent [19]

Ungarelli et al.

[11] Patent Number: 4,886,923
[45] Date of Patent: Dec. 12, 1989

[54] PROCESS FOR THE PREPARATION OF TRICYCLO 8.2.2.2 HEXADECA 4,6,10,12,13,15 HEXAENE CHLORINATED IN THE BENZENE RINGS

[75] Inventors: Raffaele Ungarelli, Novara; Maurizio A. Beretta, Milan; Loris Sogli, Novara, all of Italy

[73] Assignee: Montedison S.p.A., Milan, Italy

[21] Appl. No.: 245,325

[22] Filed: Sep. 16, 1988

[30] Foreign Application Priority Data

Sep. 18, 1987 [IT] Italy ................................ 21955 A/87

[51] Int. Cl.$^4$ ........................ C07C 17/12; C07C 25/18
[52] U.S. Cl. .................................... 570/210; 570/206; 570/207; 570/208
[58] Field of Search ............... 570/208, 210, 207, 206

[56] References Cited

U.S. PATENT DOCUMENTS

| | | | |
|---|---|---|---|
| 3,288,728 | 1/1966 | Gorham | 570/208 |
| 3,352,754 | 9/1967 | Gorham | 570/208 |
| 4,166,075 | 8/1979 | Blumenfeld | 570/210 |

*Primary Examiner*—Werren B. Lone

*Attorney, Agent, or Firm*—Stevens, Davis, Miller & Mosher

[57] ABSTRACT

A process for the chlorination of the benzene rings of tricyclo 8.2.2.2 hexadeca 4,6,10,12,13,15 hexane (or (2,2)-paracyclophane) having the formula (I):

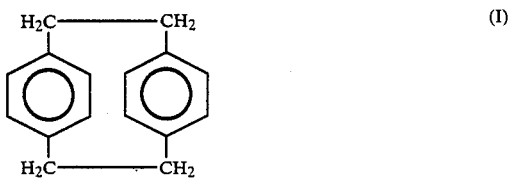

by gaseous chlorine, by operating in the presence of at least one metal chloride as a catalyst, and at least one co-catalyst having the formula V:

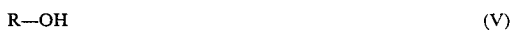

wherein
R=hydrocarbon or alkylcarboxylic radical with linear or branched chain, containing from 1 to 6 carbon atoms is taught.

9 Claims, No Drawings

PROCESS FOR THE PREPARATION OF TRICYCLO 8.2.2.2 HEXADECA 4,6,10,12,13,15 HEXAENE CHLORINATED IN THE BENZENE RINGS

DESCRIPTION OF THE INVENTION

1. Field of the Invention

The present invention relates to a process for the preparation of tricyclo 8.2.2.2 hexadeca 4,6,10,12,13,15 hexaene (or (2,2)-paracyclophane) chlorinated in the aromatic benzene rings.

More particularly, the present invention relates to a process for the preparation of tricyclo 8.2.2.2 hexadeca 4,6,10,12,13,15 hexaene chlorinated in the benzene rings, with improved selectivity characteristics, by catalytic chlorination of the starting substrate (or (2,2)-paracyclophane) having the formula (I)

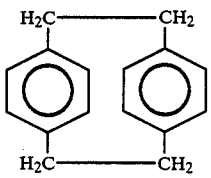

the chlorinated derivatives obtained by this process, having the formula II:

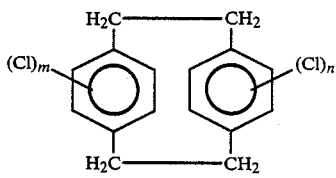

wherein the symbols m and n, which may be the same or different, represent integers from 1 to 4 and $m+n=2$ to 8, are products well known in the literature and are generally utilized as intermediates in the preparation of the corresponding poly-p.xylylene. Said polymers, and in particular poly-p.xylylene and its chlorinated derivatives, are advantageously utilized, for instance, in the form of coating films in the field of "conformal coating", obtained by application according to the vacuum vapor deposition technique in the electronic field, etc.

2. Background of the Invention

As is well known, the above-mentioned technique of vacuum vapor deposition requires the availability of a product having a high degree of purity.

Various processes have been proposed for preparing chlorinated (2,2)-paracyclophane (II) and its derivatives. However, such known processes are not fully satisfactory and are not suitable for being adopted on an industrial scale, mainly due to the low selectivity of the process.

It is well known from the literature (see for instance H. Wiegandt and P. Lantos—Industrial and Engineering Chemistry, Vol. 43, 9, pages 2167 to 2172, September 1951; R. MacMullin, Chemical Engineering Process, Vol, 44, 3, pages 183 to 188, March 1948) that at the most a dihalogenated derivative selectivity equal to about 85% is obtained by the catalytic chlorination of benzene.

It is also known (see U.S. Pat. No. 4,166,075) that the selectivity in dichloro derivatives (for example, paradichloroxylene) may be considerably improved, up to 95–96%, by the simultaneous use of a metal halide as catalyst and of an aliphatic hydrocarbon containing oxygenated functions, as co-catalyst.

DETAILED DESCRIPTION OF THE INVENTION

It has now, surprisingly, been discovered (in accordance with the present invention) that, in the case of chlorination of the (2,2)-paracyclophane by using only the above-mentioned metal chloride catalyst, it is possible to obtain a selectivity in tetrachloroparacyclophane higher than 97–98%. Said product having the formula III:

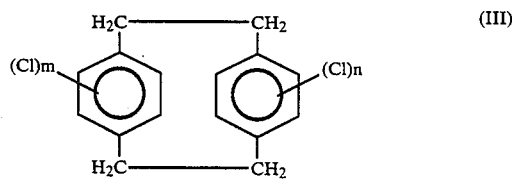

where $m+n=4$, is preferentially constituted by those isomers where $m=n=2$.

The impossibility has been also proved of obtaining dichloroparacyclophane (where $m+n=2$) with a selectivity higher than 90%, by using only the metal halide as catalyst.

Moreover, it has further been discovered that the conjoint use of the metal halide catalyst and the oxygenated hydrocarbon co-catalyst hereinafter described, allows one to obtain dichloroparacyclophane with a selectivity $\geq 96\%$. Furthermore, in the mixture of the thus-obtained dichloro-derivatives, those in which $m=n=1$, corresponding to a monochlorination of the benzene rings, are sharply prevailing ($\geq 90\%$) contrary to the disclosure in U.S. Pat. No. 4,166,075 where a high selectivity in dichloroparaxylene (95–96%) and a low selectivity (1–7%) in monochloroparaxylene are set forth.

It should be pointed out, moreover, that, owing to the aromatic mono-cyclic structure of the paraxylene substrate, there are in said reference no teaching and/or suggestion useful for solving the problem of the symmetrical chlorination (mono-chlorination) of the two benzene aromatic rings present in 2,2-paracyclophane, which is the starting material of the present invention.

In other words, the said U.S. Patent does not disclose and does not give any suggestion as to any procedure suitable for obtaining the mono-chlorinated derivative of para-xylene which constitutes a part of the (2,2)-paracyclophane molecule.

An object of the present invention, therefore, is to provide a process for preparing a chlorinated (2,2)paracyclophane having the above formula III, which process is characterized in that (2,2)-paracyclophane is subjected to chlorination in the gas phase by working in such a suspending medium and/or a halogenated organic solvent, and in the presence of at least one metal chloride, as the catalyst, having the formula IV:

wherein Me represents a metal selected from the class consisting of Fe, Sb, Al, I, Cu, Sn and p represents an integer from 1 to 5, preferably in the presence of a small amount of at least one co-catalyst having the formula V:

R—OH  (V)

wherein R represents a hydrocarbon or alkylcarboxylic radical, with linear or branched chain, containing from 1 to 6 carbon atoms.

Efficacious metal chloride catalysts have proved to be: iron, aluminum, antimony, tin, iodine, etc, chlorides or mixtures thereof.

Efficacious co-catalysts of the formula V have proved to be: methanol, ethanol, (iso)propanol, butanol, formic acid, acetic acid, propionic acid, butyric acid, or mixtures thereof.

The chlorination reaction is carried out, under stirring, at temperatures between $-70°$ and $+100°$ C., and preferably between $0°$ and $+30°$ C.

The reaction is carried out in a solution and/or dispersion of (2,2)-paracyclophane in a halogenated, linear or branched aliphatic or aromatic hydrocarbon inert solvent, preferably $CCl_4$ or $CH_2Cl_2$, at atmosphere pressure for periods of time varying from 1 to 3 hours.

The catalyst having the above formula (IV) is preferably produced in situ by the action in suspension of chlorine on the metal. The amount used is such that:

$$\frac{MeCl_p}{(2,2)\text{-paracyclophane}} = \text{about } 0.001-0.01 \text{ in moles.}$$

The co-catalyst R—OH is employed in amounts such that $$\frac{R-OH}{MeCl_p} = \text{about } 1-30 \text{ in moles.}$$

In the above definitions p has the usual meaning for Me chlorides.

In this way it is possible to obtain high selectivity values for the single derivatives chlorinated in the benzene rings having the formula II. More particularly, and by way of example, selectivity values in dichloro (2,2)-paracyclophane (G.C.titer) on the whole higher than 96% may be obtained and with a content of the derivative having $m=n=1$ equal to or higher than 90%.

In other words, the process of the present invention has proved to be particularly and selectively suitable for the mono-chlorination of the two benzene rings present in (2,2)-paracyclophane (I).

This is in contrast with what could be deduced from the above-discussed known techniques, the suggestions of which would dissuade one skilled in the art from expecting the above desirable results, especially in the case of the selective mono-chlorination ($m=n=1$) of (2,2)-paracyclophane.

The present invention may therefore be considered to be a surprising overcoming of a prejudice existing in the known art. Furthermore, the titer of the obtained product, especially of dichloro-(2,2)-paracyclophane (>96% G.C.), brings about the remarkable advantage of making it possible to use the chlorinated raw product, as such, as obtained in other processes, without the necessity of requiring burdensome and costly purification operations, etc.

By increasing the degree of halogenation of the aromatic (benzene) rings of (2,2)-paracyclophane, the selectivities of the desired species increase: for instance, when $m=n=2$ in formula II (tetrachloro (2,2)-paracyclophane), a titer (G.C.) $\geq =99\%$ has been obtained.

The starting product (2,2)-paracyclophane (tricyclo 8.2.2.2 hexadeca 4,6,10,12,13,15 hexaene) is a well known product available on the market or which is prepared according to processes well known per se.

Thus, for instance, (2,2)-paracyclophane may be obtained ("Organic Syntheses, Collective Volume 5, John Wiley and Sons Inc. New York, London, Sydney, Toronto, 1973, pages 883–886) by the Hofmann elimination reaction starting from p.methyl-benzyl-trimethyl-ammonium hydroxide obtained by reacting the corresponding bromide with silver oxide. The Hofmann elimination is carried out in the presence of a basic compound and of an inert organic solvent (e.g., toluene).

When the reaction is finished, the mixture is treated appropriately for separating the desired chlorinated product, by operating according to otherwise conventional methods, such as by removing the catalyst, distillation of the solvent, washing, etc.

The present invention is still further elucidated by the following examples, which however are to be construed as merely illustrative. The term G.C. means gas chromatography.

Example 1 has been carried out without the use of a co-catalyst (V) in order to show the selectivity improvement of the yields obtained by the use of the co-catalyst having formula (V), in the case of dichloroparacyclophane.

Examples 10 and 11 set forth the influence of the co-catalyst's presence, in the case of tetrachloroparacyclophane.

EXAMPLE 1 (Comparative)

(Preparation of dichloroparacyclophane)

36.5 g (0.175 moles) of (2,2)-paracyclophane, 0.05 g (0.0009 g-atoms) of powdered Fe, and 0.5 l of $CCl_4$, were charged into a reactor having the capacity of 1 liter. Gaseous $Cl_2$ was then fed by maintaining the temperature at $18°-20°$ C., under stirring and at atmospheric pressure.

After a period of 1 hour, 25.6 g of chlorine were bubbled into the mixture.

The solution was washed with alkaline $H_2O$ (5% of $NaHCO_3$), and the CCl4 was evaporated at a reduced pressure, thereby obtaining 48.8 g of am amorphous white solid product having the titer G.C. 89.2% of dichloroparacyclophane, corresponding to a yield of 89.8%.

The above data are listed below in Table 1.

EXAMPLES 2-9 (Preparation of dichloroparacyclophane in the presence of co-catalyst)

These examples were operated according to Example 1 up to the feeding of 70% of the desired $Cl_2$, then the co-catalyst was added and the addition of gaseous $Cl_2$ was completed.

The reactants used, the amounts thereof, and the obtained products are listed below in Table 1.

EXAMPLES 10 and 11 (Preparation of tetrachloroparacyclophane in the presence (Ex. 11) and in the absence (Ex. 10) of the co-catalyst).

These examples were operated according to Example 1 up to the feeding of 70% of the desired Cl2, the co-catalyst was added (in Example 11), and the chlorination was completed and the product recovered.

The obtained quantitative data are listed in Table 1.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

TABLE 1

| | | | | | | | | | | | | Obtained product | | |
|---|---|---|---|---|---|---|---|---|---|---|---|---|---|---|
| Example No. | PCF g. | Solvent Type | l. | Catalyst Type | g | Co-Catalyst Type | g | $Cl_2$ g. | Temperature °C. | Time h | Type | g. | Tit % GC | Yield % |
| 1 | 36.5 | $CCl_4$ | 0.5 | Fe powder | 0.05 | — | — | 25.6 | 20 | 1 | Dichloro- | 48.8 | 89.2 | 89.8 |
| 2 | " | " | " | " | " | Acet. Ac | 0.5 | 25.5 | 18 | 1.25 | " | 48.5 | 96.5 | 96.6 |
| 3 | " | $CH_2Cl_2$ | " | " | " | Methanol | 0.55 | " | " | " | " | 47.9 | 96.1 | 94.9 |
| 4 | " | " | " | Sb | 0.11 | Ethanol | 0.8 | " | " | 1 | " | 47.3 | 96 | 93.7 |
| 5 | " | " | " | Al | 0.03 | Isoprop | 1.5 | " | 20 | 1.5 | " | 46.4 | 96.3 | 92.2 |
| 6 | " | $CCl_4$ | " | $I_2$ | 0.11 | Methanol | 0.55 | " | 18 | " | " | 46.2 | 96.4 | 91.9 |
| 7 | 20.8 | " | " | Sn | " | " | " | 14.5 | " | 3 | " | 25.9 | 95.9 | 89.7 |
| 8 | " | " | " | Cu | 0.03 | Ethanol | 0.5 | " | 20 | 2 | " | 26.1 | 96 | 90.4 |
| 9 | 36.5 | " | " | Fe Wool | 0.05 | Acet. Ac | 0.5 | 25.5 | 18 | 1.25 | " | 48.7 | 96.7 | 97.1 |
| 10 | " | " | " | Fe powder | 0.05 | — | — | 50.5 | 20 | 1.5 | Tetrachloro PCF | 60.9 | 99.1 | 99.4 |
| 11 | " | " | " | Fe Wool | " | " | " | 50.5 | " | 1.25 | " | 60.8 | 99 | 99.4 |

PCF = Paracyclophane

What is claimed is:

1. A process for preparing a chlorinated (2,2)-paracyclophane having formula II:

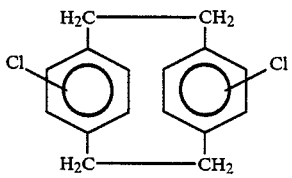

(II)

comprise subjecting (2,2)-paracyclophane (PCF) to gaseous chlorination in a halogenated organic suspending or solvent medium and in the presence of at least one metal chloride catalyst having formula IV:

  (UV)

where Me is selected from the group consisting of Fe, Sb, Al, I, Cu and Sn and p represents an integer from 1 to 5 and in the presence of at least one co-catalyst having formula R—OH, where R represents a hydrocarbyl or alkylcarboxylic radical, having a linear or a branched chain, containing from 1 to 6 C atoms, the temperature being substantially from −70° C. to 100 ° C., the pressure being substantially at an atmospheric level and the chlorine: (PCP) ratio being equal to or lower than 0.7 by weight.

2. The process according to claim 1, wherein the reaction is carried out in a suspending medium selected from $CCl_4$ and $CH_2Cl_2$, at a temperature between 0° C. and +30° C. and at about atmospheric pressure.

3. The process according to claim 1, wherein the metal chloride catalyst having formula IV is prepared in situ by the action of gaseous chlorine on the metal in the reaction medium suspension 4. The process according to claim 1, wherein the molecular ratio of the metal chloride catalyst having formula IV with respect to the starting (2,2)-paracyclophane is between about 0.001 and 0.01 and the molar ratio of the co-catalyst with respect to the metal chloride catalyst having formula IV is between about 1 and 30.

5. The process according to claim 1, wherein the metal chloride catalyst having formula IV is ferric chloride.

6. The process according to claim 1, wherein the co-catalyst is selected from the class consisting of methyl alcohol, ethyl alcohol, isopropyl alcohol, acetic acid and mixtures thereof.

7. Chlorinated (2,2)-paracyclophane having formula II as defined in claim 1 that is mono-chlorinated in each of the benzene rings, when obtained by the process defined in claim 1.

8. Chlorinated (2,2)-paracyclophane having formula II as defined in claim 1 that is di-chlorinated in each of the benzene rings, when obtained by the process defined in claim 1.

9. The process according to claim 1, wherein the reaction is carried out in a chlorinated organic solvent at a temperature between 0° C. and +30° C. and at about atmospheric pressure.

* * * * *